United States Patent
Wen

(10) Patent No.: US 10,357,336 B2
(45) Date of Patent: Jul. 23, 2019

(54) SYSTEMS AND METHODS FOR FABRICATING DENTAL APPLIANCES OR SHELLS

(71) Applicant: uLab Systems, Inc., Menlo Park, CA (US)

(72) Inventor: Huafeng Wen, Redwood Shores, CA (US)

(73) Assignee: uLab Systems, Inc., Redwood City, CA (US)

(*) Notice: Subject to any disclaimer, the term of this patent is extended or adjusted under 35 U.S.C. 154(b) by 157 days.

(21) Appl. No.: 15/230,251

(22) Filed: Aug. 5, 2016

(65) Prior Publication Data
US 2017/0100211 A1 Apr. 13, 2017

Related U.S. Application Data

(60) Provisional application No. 62/238,539, filed on Oct. 7, 2015.

(51) Int. Cl.
*A61C 7/00* (2006.01)
*A61C 7/08* (2006.01)
*A61C 13/34* (2006.01)

(52) U.S. Cl.
CPC ............ *A61C 7/002* (2013.01); *A61C 7/08* (2013.01); *A61C 13/34* (2013.01)

(58) Field of Classification Search
CPC ............ A61C 7/002; A61C 7/08; A61C 13/34
USPC ................................................. 700/97, 118
See application file for complete search history.

(56) References Cited

U.S. PATENT DOCUMENTS

| | | |
|---|---|---|
| 4,068,379 A | 1/1978 | Miller et al. |
| 4,889,485 A | 12/1989 | Iida |
| 4,983,334 A | 1/1991 | Adell |
| 5,055,039 A | 10/1991 | Abbatte et al. |
| 5,186,623 A | 2/1993 | Breads et al. |
| 5,691,905 A | 11/1997 | Dehoff et al. |
| 5,975,893 A | 11/1999 | Chishti et al. |
| 6,183,248 B1 | 2/2001 | Chishti et al. |
| 6,210,162 B1 | 4/2001 | Chishti et al. |
| 6,217,325 B1 | 4/2001 | Chishti et al. |
| 6,227,850 B1 | 5/2001 | Chishti et al. |
| 6,227,851 B1 | 5/2001 | Chishti et al. |
| 6,299,440 B1 | 10/2001 | Phan et al. |
| 6,309,215 B1 | 10/2001 | Phan et al. |
| 6,315,553 B1 * | 11/2001 | Sachdeva ............ A61C 7/00 433/213 |
| 6,390,812 B1 | 5/2002 | Chishti et al. |

(Continued)

FOREIGN PATENT DOCUMENTS

| | | |
|---|---|---|
| WO | WO 2006/050452 | 5/2006 |
| WO | WO 2006/096558 | 9/2006 |

(Continued)

*Primary Examiner* — Chun Cao
(74) *Attorney, Agent, or Firm* — Levine Bagade Han LLP

(57) ABSTRACT

Systems and methods are disclosed for cutting and trimming dental molds and oral appliances by receiving a digital model of teeth, determining a cutting loop path and applying a drape wall to the cutting loop to generate a simplified tooth base in a dental mold having an inner arch curve and an outer arch curve. The oral appliance may be formed on the dental mold and a cutter may be applied using a sweeping motion across the inner and outer arch curves.

27 Claims, 10 Drawing Sheets

(56) References Cited

U.S. PATENT DOCUMENTS

| | | |
|---|---|---|
| 6,398,548 B1 | 6/2002 | Chishti et al. |
| 6,454,565 B2 | 9/2002 | Phan et al. |
| 6,463,344 B1 | 10/2002 | Pavloskaia |
| 6,471,511 B1 | 10/2002 | Chishti et al. |
| 6,485,298 B2 | 11/2002 | Chishti et al. |
| 6,488,499 B1 | 12/2002 | Miller |
| 6,524,101 B1 | 2/2003 | Phan et al. |
| 6,554,611 B2 | 4/2003 | Chishti et al. |
| 6,572,372 B1 | 6/2003 | Phan et al. |
| 6,582,227 B2 | 6/2003 | Phan et al. |
| 6,602,070 B2 | 8/2003 | Miller et al. |
| 6,607,382 B1 | 8/2003 | Kuo et al. |
| 6,626,666 B2 | 9/2003 | Chishti et al. |
| 6,629,840 B2 | 10/2003 | Chishti et al. |
| 6,682,346 B2 | 1/2004 | Chishti et al. |
| 6,688,885 B1 | 2/2004 | Sachdeva et al. |
| 6,699,037 B2 | 3/2004 | Chishti et al. |
| 6,702,575 B2 | 3/2004 | Hilliard |
| 6,705,861 B2 | 3/2004 | Chishti et al. |
| 6,705,863 B2 | 3/2004 | Phan et al. |
| 6,722,880 B2 | 4/2004 | Chishti et al. |
| 6,729,876 B2 | 5/2004 | Chishti et al. |
| 6,761,560 B2 | 7/2004 | Miller |
| 6,786,721 B2 | 9/2004 | Chishti et al. |
| 6,802,713 B1 | 10/2004 | Chishti et al. |
| 6,830,450 B2 | 12/2004 | Knopp et al. |
| 6,846,179 B2 | 1/2005 | Chapouland et al. |
| 6,857,429 B2 | 2/2005 | Eubank |
| 6,886,566 B2 | 5/2005 | Eubank |
| 6,964,564 B2 | 11/2005 | Phan et al. |
| 7,011,517 B2 | 3/2006 | Nicozisis |
| 7,029,275 B2 | 4/2006 | Rubbert et al. |
| 7,037,108 B2 | 5/2006 | Chishti et al. |
| 7,056,115 B2 | 6/2006 | Phan et al. |
| 7,059,850 B1 | 6/2006 | Phan et al. |
| 7,063,533 B2 | 6/2006 | Phan et al. |
| 7,092,784 B1 | 8/2006 | Simkins |
| 7,104,790 B2 | 9/2006 | Cronauer |
| 7,121,825 B2 | 10/2006 | Chishti et al. |
| 7,125,248 B2 | 10/2006 | Phan et al. |
| 7,134,874 B2 | 11/2006 | Chishti et al. |
| 7,192,275 B2 | 3/2007 | Miller |
| 7,320,592 B2 | 1/2008 | Chishti et al. |
| 7,326,051 B2 | 2/2008 | Miller |
| 7,331,783 B2 | 2/2008 | Chishti et al. |
| 7,347,688 B2 | 3/2008 | Kopelman et al. |
| 7,416,407 B2 | 8/2008 | Cronauer |
| 7,434,582 B2 | 10/2008 | Eubank |
| 7,476,100 B2 | 1/2009 | Kuo |
| 7,553,157 B2 | 6/2009 | Abolfathi et al. |
| 7,559,328 B2 | 7/2009 | Eubank |
| 7,578,673 B2 | 8/2009 | Wen et al. |
| 7,590,462 B2 | 9/2009 | Rubbert et al. |
| 7,637,262 B2 | 12/2009 | Bailey |
| 7,641,828 B2 | 1/2010 | Desimone et al. |
| 7,658,610 B2 | 2/2010 | Knopp |
| 7,771,195 B2 | 8/2010 | Knopp et al. |
| 7,802,987 B1 | 9/2010 | Phan |
| 7,824,180 B2 | 11/2010 | Abolfathi et al. |
| 7,826,646 B2 * | 11/2010 | Pavlovskaia ............. A61C 5/00 382/128 |
| 7,841,858 B2 | 11/2010 | Knopp et al. |
| 7,854,609 B2 | 12/2010 | Chen et al. |
| 7,878,801 B2 | 2/2011 | Abolfathi et al. |
| 7,878,804 B2 | 2/2011 | Korytov et al. |
| 7,878,805 B2 | 2/2011 | Moss et al. |
| 7,883,334 B2 | 2/2011 | Li et al. |
| 7,901,207 B2 | 3/2011 | Knopp et al. |
| 7,905,724 B2 | 3/2011 | Kuo et al. |
| 7,914,283 B2 | 3/2011 | Kuo |
| 7,942,672 B2 | 5/2011 | Kuo |
| 7,943,079 B2 | 5/2011 | Desimone et al. |
| 7,957,824 B2 | 6/2011 | Boronvinskih et al. |
| 8,001,972 B2 | 8/2011 | Eubank |
| 8,033,282 B2 | 10/2011 | Eubank |
| 8,038,444 B2 | 10/2011 | Kitching et al. |
| 8,070,487 B2 | 12/2011 | Chishti et al. |
| 8,105,080 B2 | 1/2012 | Chishti et al. |
| 8,123,519 B2 | 2/2012 | Schultz |
| 8,152,518 B2 | 4/2012 | Kuo |
| 8,235,713 B2 | 8/2012 | Phan et al. |
| 8,272,866 B2 | 9/2012 | Chun et al. |
| 8,292,617 B2 | 10/2012 | Brandt et al. |
| 8,303,302 B2 | 11/2012 | Teasdale |
| 8,348,665 B2 | 1/2013 | Kuo |
| 8,356,993 B1 | 1/2013 | Marston |
| 8,401,686 B2 | 3/2013 | Moss et al. |
| 8,401,826 B2 | 3/2013 | Cheng et al. |
| 8,439,672 B2 | 5/2013 | Matov et al. |
| 8,439,673 B2 | 5/2013 | Korytov et al. |
| 8,444,412 B2 | 5/2013 | Baughman et al. |
| 8,469,706 B2 | 6/2013 | Kuo |
| 8,496,474 B2 | 7/2013 | Chishti et al. |
| 8,517,726 B2 | 8/2013 | Kakavand et al. |
| 8,535,580 B2 | 9/2013 | Puttler et al. |
| 8,562,337 B2 | 10/2013 | Kuo et al. |
| 8,562,340 B2 | 10/2013 | Chishti et al. |
| 8,690,568 B2 | 4/2014 | Chapoulaud et al. |
| 8,708,697 B2 | 4/2014 | Li et al. |
| 8,734,149 B2 | 5/2014 | Phan et al. |
| 8,734,150 B2 | 5/2014 | Chishti et al. |
| 8,738,165 B2 | 5/2014 | Cinader, Jr. et al. |
| 8,765,031 B2 | 7/2014 | Li et al. |
| 8,777,611 B2 | 7/2014 | Cios |
| 8,780,106 B2 | 7/2014 | Chishti et al. |
| 8,807,999 B2 | 8/2014 | Kuo et al. |
| 8,858,226 B2 | 10/2014 | Phan et al. |
| 8,864,493 B2 | 10/2014 | Leslie-Martin et al. |
| 8,899,976 B2 | 12/2014 | Chen et al. |
| 8,936,464 B2 | 1/2015 | Kopelman |
| 8,944,812 B2 | 2/2015 | Kuo |
| 8,961,173 B2 | 2/2015 | Miller |
| 8,986,003 B2 | 3/2015 | Valoir |
| 8,992,215 B2 | 3/2015 | Chapoulaud et al. |
| 9,004,915 B2 | 4/2015 | Moss et al. |
| 9,022,781 B2 | 5/2015 | Kuo et al. |
| 9,026,238 B2 * | 5/2015 | Kraemer ............. A61C 13/0022 700/98 |
| 9,060,829 B2 | 6/2015 | Sterental et al. |
| 9,107,722 B2 | 8/2015 | Matov et al. |
| 9,119,691 B2 | 9/2015 | Namiranian et al. |
| 9,161,823 B2 | 10/2015 | Morton et al. |
| 9,161,824 B2 | 10/2015 | Chishti et al. |
| 9,204,942 B2 | 12/2015 | Phan et al. |
| 9,241,774 B2 | 1/2016 | Li et al. |
| 9,301,814 B2 | 4/2016 | Kaza et al. |
| 9,320,575 B2 | 4/2016 | Chishti et al. |
| 9,333,052 B2 | 5/2016 | Miller |
| 9,345,557 B2 | 5/2016 | Anderson et al. |
| 9,351,809 B2 | 5/2016 | Phan et al. |
| 9,375,300 B2 | 6/2016 | Matov et al. |
| 2002/0010568 A1 | 1/2002 | Rubbert et al. |
| 2002/0025503 A1 | 2/2002 | Chapoulaud et al. |
| 2002/0094503 A1 | 7/2002 | Chishti et al. |
| 2003/0008259 A1 | 1/2003 | Kuo et al. |
| 2003/0190576 A1 | 10/2003 | Phan et al. |
| 2004/0152036 A1 | 8/2004 | Abolfathi |
| 2004/0166456 A1 | 8/2004 | Chishti et al. |
| 2004/0166462 A1 | 8/2004 | Phan et al. |
| 2004/0166463 A1 | 8/2004 | Wen et al. |
| 2004/0197728 A1 | 10/2004 | Abolfathi et al. |
| 2004/0202983 A1 | 10/2004 | Tricca et al. |
| 2005/0010450 A1 | 1/2005 | Hultgren et al. |
| 2005/0153255 A1 | 7/2005 | Sporbert et al. |
| 2005/0244782 A1 | 11/2005 | Chishti et al. |
| 2006/0003283 A1 | 1/2006 | Miller et al. |
| 2006/0035197 A1 | 2/2006 | Hishimoto |
| 2006/0068353 A1 | 3/2006 | Abolfathi et al. |
| 2006/0078840 A1 | 4/2006 | Robson |
| 2006/0078841 A1 | 4/2006 | Desimone et al. |
| 2006/0093982 A1 | 5/2006 | Wen |
| 2006/0099546 A1 | 5/2006 | Bergersen |
| 2006/0115785 A1 | 6/2006 | Li et al. |
| 2006/0177789 A1 | 8/2006 | O'Bryan |

(56) References Cited

U.S. PATENT DOCUMENTS

| | | |
|---|---|---|
| 2006/0188834 A1 | 8/2006 | Hilliard |
| 2006/0199142 A1 | 9/2006 | Liu et al. |
| 2006/0223022 A1 | 10/2006 | Solomon |
| 2006/0223023 A1 | 10/2006 | Lai et al. |
| 2006/0275731 A1 | 12/2006 | Wen et al. |
| 2007/0003907 A1 | 1/2007 | Chishti et al. |
| 2007/0283967 A1 | 12/2007 | Bailey |
| 2008/0032248 A1 | 2/2008 | Kuo |
| 2008/0044786 A1 | 2/2008 | Kalili |
| 2008/0050692 A1 | 2/2008 | Hilliard |
| 2008/0051650 A1 | 2/2008 | Massie et al. |
| 2008/0057462 A1 | 3/2008 | Kitching et al. |
| 2008/0076086 A1 | 3/2008 | Kitching et al. |
| 2008/0085487 A1 | 4/2008 | Kuo et al. |
| 2008/0118882 A1 | 5/2008 | Su |
| 2008/0141534 A1 | 6/2008 | Hilliard |
| 2008/0182220 A1 | 7/2008 | Chishti et al. |
| 2008/0206702 A1 | 8/2008 | Hedge et al. |
| 2008/0215176 A1* | 9/2008 | Borovinskih .......... G06Q 50/04 700/117 |
| 2008/0248438 A1 | 10/2008 | Desimone et al. |
| 2008/0248443 A1 | 10/2008 | Chisti et al. |
| 2008/0261165 A1 | 10/2008 | Steingart et al. |
| 2008/0268400 A1 | 10/2008 | Moss et al. |
| 2009/0081604 A1 | 3/2009 | Fisher |
| 2009/0191502 A1 | 7/2009 | Cao et al. |
| 2009/0269714 A1 | 10/2009 | Knopp |
| 2009/0280450 A1 | 11/2009 | Kuo |
| 2009/0291407 A1 | 11/2009 | Kuo |
| 2009/0291408 A1 | 11/2009 | Stone-Collonge et al. |
| 2010/0055635 A1 | 3/2010 | Kakavand |
| 2010/0167225 A1 | 7/2010 | Kuo |
| 2010/0280798 A1 | 11/2010 | Pattijn et al. |
| 2011/0005527 A1 | 1/2011 | Andrew et al. |
| 2011/0015591 A1 | 1/2011 | Hanson et al. |
| 2011/0020761 A1 | 1/2011 | Kalili |
| 2011/0039223 A1 | 2/2011 | Li et al. |
| 2011/0114100 A1 | 5/2011 | Alvarez et al. |
| 2011/0123944 A1 | 5/2011 | Knopp et al. |
| 2011/0129786 A1 | 6/2011 | Chun et al. |
| 2011/0165533 A1 | 7/2011 | Li et al. |
| 2011/0269092 A1 | 11/2011 | Kuo et al. |
| 2011/0281229 A1 | 11/2011 | Abolfathi |
| 2012/0123577 A1 | 5/2012 | Chapoulaud et al. |
| 2012/0150494 A1 | 6/2012 | Anderson et al. |
| 2012/0186589 A1 | 7/2012 | Singh |
| 2012/0199136 A1 | 8/2012 | Urbano |
| 2012/0214121 A1 | 8/2012 | Greenberg |
| 2012/0225399 A1 | 9/2012 | Teasdale |
| 2012/0225400 A1 | 9/2012 | Chishti et al. |
| 2012/0244488 A1 | 9/2012 | Chishti et al. |
| 2012/0270173 A1 | 10/2012 | Pumphrey et al. |
| 2012/0288818 A1 | 11/2012 | Vendittelli |
| 2013/0052625 A1 | 2/2013 | Wagner |
| 2013/0078593 A1 | 3/2013 | Andreiko |
| 2013/0081271 A1 | 4/2013 | Farzin-Nia et al. |
| 2013/0095446 A1 | 4/2013 | Andreiko et al. |
| 2013/0122445 A1 | 5/2013 | Marston |
| 2013/0122448 A1 | 5/2013 | Kitching |
| 2013/0157213 A1 | 6/2013 | Arruda |
| 2013/0201450 A1 | 8/2013 | Bailey et al. |
| 2013/0204583 A1 | 8/2013 | Matov et al. |
| 2013/0230819 A1 | 9/2013 | Arruda |
| 2013/0236848 A1 | 9/2013 | Arruda |
| 2013/0266906 A1 | 10/2013 | Soo |
| 2013/0302742 A1 | 11/2013 | Li et al. |
| 2013/0323665 A1 | 12/2013 | Dinh et al. |
| 2013/0325431 A1 | 12/2013 | See et al. |
| 2014/0067335 A1 | 3/2014 | Andreiko et al. |
| 2014/0072926 A1 | 3/2014 | Valoir |
| 2014/0076332 A1 | 3/2014 | Luco |
| 2014/0124968 A1 | 5/2014 | Kim |
| 2014/0172375 A1 | 6/2014 | Grove |
| 2014/0193767 A1 | 7/2014 | Li et al. |
| 2014/0229878 A1 | 8/2014 | Wen et al. |
| 2014/0242532 A1 | 8/2014 | Arruda |
| 2014/0272757 A1 | 9/2014 | Chishti |
| 2014/0287376 A1 | 9/2014 | Hultgren et al. |
| 2014/0288894 A1 | 9/2014 | Chishti et al. |
| 2014/0315153 A1 | 10/2014 | Kitching et al. |
| 2014/0315154 A1 | 10/2014 | Jung et al. |
| 2014/0329194 A1 | 11/2014 | Sachdeva et al. |
| 2014/0349242 A1 | 11/2014 | Phan et al. |
| 2014/0363779 A1 | 12/2014 | Kopelman |
| 2014/0370452 A1 | 12/2014 | Tseng |
| 2015/0004553 A1 | 1/2015 | Li et al. |
| 2015/0004554 A1 | 1/2015 | Cao et al. |
| 2015/0018956 A1 | 1/2015 | Steinmann et al. |
| 2015/0044623 A1 | 2/2015 | Rundlett |
| 2015/0044627 A1 | 2/2015 | German |
| 2015/0093713 A1 | 4/2015 | Chen et al. |
| 2015/0093714 A1 | 4/2015 | Kopelman |
| 2015/0125802 A1 | 5/2015 | Tal |
| 2015/0128421 A1 | 5/2015 | Mason et al. |
| 2015/0157421 A1 | 6/2015 | Martz et al. |
| 2015/0182321 A1 | 7/2015 | Karazivan et al. |
| 2015/0216626 A1 | 8/2015 | Ranjbar |
| 2015/0216627 A1 | 8/2015 | Kopelman |
| 2015/0238282 A1 | 8/2015 | Kuo et al. |
| 2015/0238283 A1 | 8/2015 | Tanugula et al. |
| 2015/0238284 A1 | 8/2015 | Wu et al. |
| 2015/0245887 A1 | 9/2015 | Izugami et al. |
| 2015/0254410 A1 | 9/2015 | Sterental et al. |
| 2015/0265376 A1 | 9/2015 | Kopelman |
| 2015/0289949 A1 | 10/2015 | Moss et al. |
| 2015/0289950 A1 | 10/2015 | Khan |
| 2015/0305830 A1 | 10/2015 | Howard et al. |
| 2015/0320518 A1 | 11/2015 | Namiranian et al. |
| 2015/0320532 A1 | 11/2015 | Matty et al. |
| 2015/0335399 A1 | 11/2015 | Caraballo |
| 2015/0335404 A1 | 11/2015 | Webber et al. |
| 2015/0336299 A1 | 11/2015 | Tanugula et al. |
| 2015/0342464 A1 | 12/2015 | Wundrak et al. |
| 2015/0351871 A1 | 12/2015 | Chishti et al. |
| 2015/0359609 A1 | 12/2015 | Khan |
| 2015/0366637 A1 | 12/2015 | Kopelman et al. |
| 2015/0366638 A1 | 12/2015 | Kopelman et al. |
| 2016/0000527 A1 | 1/2016 | Arruda |
| 2016/0008095 A1 | 1/2016 | Matov et al. |
| 2016/0008097 A1 | 1/2016 | Chen et al. |
| 2016/0051341 A1 | 2/2016 | Webber |
| 2016/0051342 A1 | 2/2016 | Phan et al. |
| 2016/0051348 A1 | 2/2016 | Boerjes et al. |
| 2016/0067013 A1 | 3/2016 | Morton et al. |
| 2016/0067014 A1 | 3/2016 | Kottemann et al. |
| 2016/0074137 A1 | 3/2016 | Kuo et al. |
| 2016/0106521 A1 | 4/2016 | Tanugula et al. |
| 2016/0120617 A1 | 5/2016 | Lee |
| 2016/0120621 A1 | 5/2016 | Li et al. |
| 2016/0128803 A1 | 5/2016 | Webber et al. |
| 2016/0135924 A1 | 5/2016 | Choi et al. |
| 2016/0135926 A1 | 5/2016 | Djamchidi |
| 2016/0135927 A1 | 5/2016 | Boltunov et al. |
| 2016/0157961 A1 | 6/2016 | Lee |
| 2016/0175068 A1 | 6/2016 | Cai et al. |
| 2016/0175069 A1 | 6/2016 | Korytov et al. |
| 2016/0184129 A1 | 6/2016 | Liptak et al. |
| 2016/0193014 A1 | 7/2016 | Morton et al. |
| 2016/0256240 A1 | 9/2016 | Shivapuja et al. |
| 2017/0100207 A1 | 4/2017 | Wen |
| 2017/0100208 A1 | 4/2017 | Wen |
| 2017/0100209 A1 | 4/2017 | Wen |
| 2017/0100210 A1 | 4/2017 | Wen |
| 2017/0100214 A1 | 4/2017 | Wen |
| 2018/0014912 A1 | 1/2018 | Radmand |
| 2018/0078335 A1 | 3/2018 | Falkel |
| 2018/0078343 A1 | 3/2018 | Falkel |
| 2018/0078344 A1 | 3/2018 | Falkel |
| 2018/0078347 A1 | 3/2018 | Falkel |

FOREIGN PATENT DOCUMENTS

| | | |
|---|---|---|
| WO | WO 2009/068892 | 6/2009 |
| WO | WO 2016/004415 | 1/2016 |

(56) References Cited

FOREIGN PATENT DOCUMENTS

| WO | WO 2017/062207 | 4/2017 |
| WO | WO 2017/062208 | 4/2017 |
| WO | WO 2017/062209 | 4/2017 |
| WO | WO 2017/062210 | 4/2017 |
| WO | WO 2018/057622 | 3/2018 |
| WO | WO 2018/118200 | 6/2018 |

* cited by examiner

SYSTEMS AND METHODS FOR FABRICATING DENTAL APPLIANCES OR SHELLS

CROSS-REFERENCE TO RELATED APPLICATIONS

This application claims the benefit of priority to U.S. Provisional Application No. 62/238,539 filed Oct. 7, 2015, which is incorporated herein by reference in its entirety.

FIELD OF THE INVENTION

The present invention relates to methods and apparatus for fabricating dental appliances. More particularly, the present invention relates to methods and apparatus for forming and cutting of molds used in fabricating oral appliances in an automated process and with a single machine.

BACKGROUND OF THE INVENTION

Conventionally, braces use brackets connected by wires to encourage teeth to move but more people are having success with clear orthodontic devices called aligners which are a series of tight-fitting custom-made retainers that slip over the teeth. Once a dentist or orthodontist decides how to correct a patient's bite, they make a plan for moving teeth. Patients are then fitted for several versions that make slight adjustments to move the teeth over the treatment time. Aligners made from a clear plastic or acrylic material and fit tightly over the teeth, but can be removed for eating, brushing, and flossing. Patients wear a new aligner every few weeks to continue moving the teeth into the desired position.

Treatment time with invisible teeth aligners is based on how much the teeth need to be moved or rotated. The more the patient bite is off or the more crooked the teeth, the longer it will take. Treatment usually takes between 10 and 24 months. An adult who had braces as a child may need teeth aligners for as little as 10 weeks.

Conventional aligners are typically fabricated at a central lab remote from the dental offices and such systems cause delays and fail to offer real-time, instant treatment for patients. Moreover, the manufacturing of the aligners are time-consuming and require multiple steps in fabricating the molds used to create the aligners as well as the aligners themselves.

Therefore, there remains a need for cost-effective systems which enable the modeling and fabrication of the molds and aligners directly at the dental office locations for providing real-time, instant treatment.

SUMMARY OF THE INVENTION

Systems and methods are disclosed for cutting and trimming dental molds and oral appliances by receiving a digital model of teeth, determining a cutting loop path and applying a drape wall to the cutting loop to generate a simplified tooth base in a dental mold having an inner arch curve and an outer arch curve. The oral appliance may be formed on the dental mold and a cutter may be applied using a single sweeping motion across the inner and outer arch curves.

The system enables an easy way to cut and trim tooth models. The system allows close control by the treating professional at each stage by allowing specific movements from one stage to the next stage. The system can form aligners quickly and efficiently due to the drape wall simplification. The CNC machines can manufacture each shell as a custom device for many stages of tooth movement. The mold can be cut/trimmed using inexpensive 2D cutting machines, if needed. Additionally, the resulting oral appliances (aligners, shells, etc. can be removed from the positive mold with minimal force, reducing risk of shell tear from excessive removal force.

Generally, one embodiment for a method of forming an oral appliance may comprise receiving a digital model of a patient's dentition, calculating a rule-based cutting loop path on the model for determining a path for trimming a mold replicating the patient's dentition, applying a drape wall from the cutting loop on the model to reduce a complexity of the model, determining a position of a cutting instrument relative to the mold for trimming the mold, generating a computer numerical control code based on the drape wall and position of the cutting instrument, and fabricating the mold based on the generated computer numerical control code.

Another embodiment for a method of forming an oral appliance may generally comprise receiving a digital model of a patient's dentition, calculating a rule-based cutting loop path on the model for determining a path for trimming a mold replicating the patient's dentition, applying a drape wall from the cutting loop on the model to reduce a complexity of the model, determining a predetermined height of a base of the model, generating a computer numerical control code of the model, and fabricating the mold based on the generated computer numerical control code.

BRIEF DESCRIPTION OF THE DRAWINGS

The following description of the figures of specific embodiments of the invention is merely exemplary in nature and is not intended to limit the present teachings, their application or uses. Throughout the drawings, corresponding reference numerals indicate like or corresponding parts and features.

DETAILED DESCRIPTION OF THE INVENTION

Figure 1:
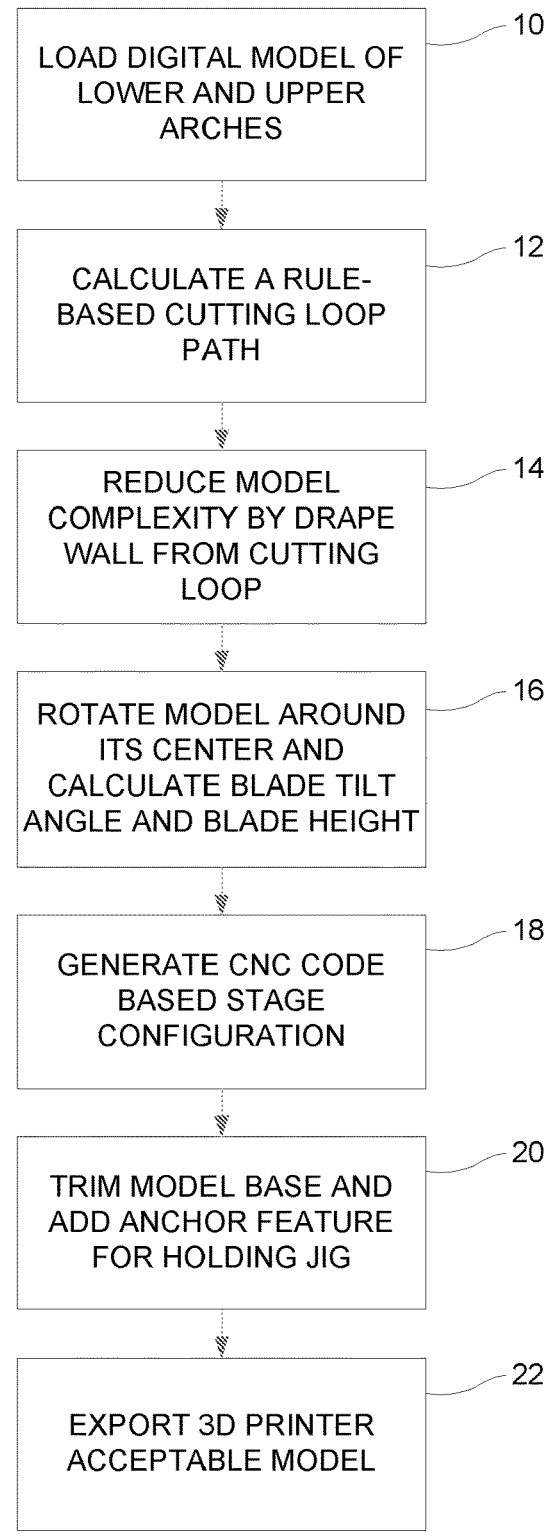
FIG. 1 shows an exemplary process for fabricating an oral appliance.

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In fabricating oral or dental appliances which are used to treat malocclusions in a patient's dentition, the oral appliance may be initially formed via, e.g., thermal forming or three-dimensional (3D) printing techniques. Once formed, the oral appliance may require further processing to trim excess material for ensuring a good fit on the patient. However, trimming this excess is typically a time-consuming process which requires a separate step after forming the appliance.

In one embodiment, the forming and cutting of the oral appliance may be accomplished in an automated process and with a single machine. Generally, a patient's scanned dentition may be used to create one or more molds of the dentition where each subsequent mold is configured to subsequently follow a corrective path for one or more teeth for correcting malocclusions in the dentition. Each of the one or more molds may be used as a mold for thermal forming or 3D printing a corresponding oral appliance upon the molds. The resulting oral appliances may be used in sequence to move the dentition for correcting the malocclusions.

FIG. 1 shows an exemplary process for utilizing computerized or computer numerical control (CNC) for fabricating the oral appliances. Typical CNC systems and end-to-end component design is highly automated using computer-aided design (CAD) and computer-aided manufacturing (CAM) dental software. The process begins by loading digital models of the lower and upper arches 10 of the subject's dentition into a computer system having a processor. This may involve capturing the 3D representation of the surfaces, e.g. external contours, of a patient's dentition for correcting one or more malocclusions. For this purpose, the subject may be scanned using a 3D scanner, e.g. a hand-held laser scanner, and the collected data can then be used to construct a digital, three dimensional model of the body part of the subject. Alternatively, the patient-specific images can be provided by a technician or medical practitioner by scanning the subject or part thereof. Such images can then be used as or converted into a three-dimensional representation of the subject, or part thereof.

With the digital model of the subject's dentition loaded into the computer system, the process then calculates a rule-based cutting loop path 12 on the digital model for determining a path along which the CNC machine may follow for trimming the mold upon which the oral appliance is fabricated. Once the cutting loop path has been determined, the process may then reduce the model complexity by applying a drape wall 14 (as described in farther detail below) which digitally extends from the cutting loop path towards a bottom of the mold model (e.g., away from the portion of the appliance which contacts the teeth and towards the portion of the appliance which extends towards the gurus). The drape wall functions by defining a region of the oral appliance which can be ignored since this portion is to be removed or trimmed.

The digital model may then be rotated around its center in relation to a reference plane in order to calculate a cutting blade tilt angle and blade height 16 (relative to the reference plane) which may be applied during the actual trimming procedure. With this information, the code to be sent to the CNC machine may be generated based on the stage configuration to be utilized 18. A physical mold base to be used in the processing procedure may be trimmed and one or more anchoring features may be incorporated into the mold base for securing a holding jig which may be used to secure the oral appliance 20 to the mold base. The completed digital model may then be exported as, e.g., a 3D printer acceptable model 22, for printing the oral appliance or mold upon which an oral appliance may be formed.

Figure 2:
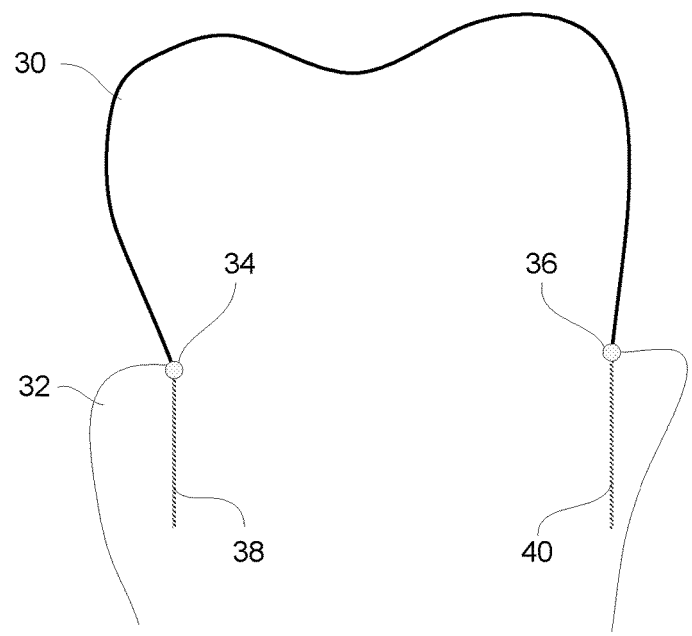
FIGS. 2 and 3 show side views of an exemplary process of defining a trim line between opposed dots on a digital model of the oral appliance.
Figure 3:
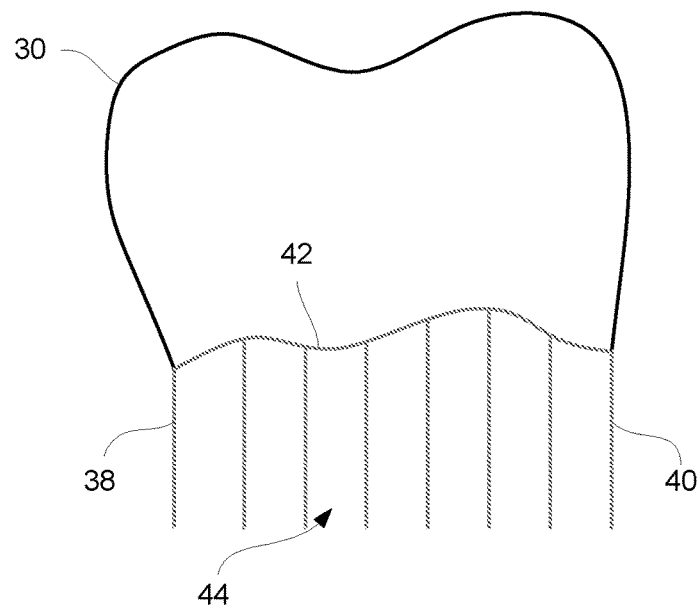

FIGS. 2 and 3 show side views of a portion of a digital model of a patient's dentition showing a tooth 30 and gums 32, as an example. In calculating a rule-based cutting loop path 12, as shown in FIG. 1 above, the scanned image of the patient's dentition may be processed to identify the interface areas between the teeth and gums 32. One or more markers 34, 36 may be digitally placed on the model at these interface regions such that the markers 34, 36 are opposed to one another on the model. A boundary or trim line 42 may then be defined to extend between the markers 34, 36 such that the trim line 42 follows the border between the teeth and gums. With the trim line 42 identified on the model, a series of drop lines 38, 40 which are parallel to one another and spaced apart, e.g., uniformly, relative to one another may be formed to begin from the trim line 42 and extend away from the trim line 42 and away from the dentition in a straight path. This base region 44 formed by the drop lines 38, 40 below the trim line 42, i.e., away from or opposite to the dentition, may be identified and demarcated as a region to be removed from the mold.

To ensure that the height of the mold including the base region 44 does not excessively stretch the material forming the oral appliance, the system may be used to determine the lowest point (relative to the trim line 42 and appliance 30) for trimming the entire mold just above this identified lowest point. In one embodiment, the trimming may be done with a predetermined margin, e.g., 2 mm, above the lowest identified point. The base region wall can also be tapered slightly based on the height of the base region wall so that the width of the base region 44 tapers from a larger width adjacent to the trim line 42 down to a relatively smaller width away from the trim line 42. The resulting mold formed from the dentition (or corrected dentition) is shown in the side view of FIG. 3 where the base region 44 has a minimum height of the predetermined margin, e.g., 2 mm.

Figure 4:
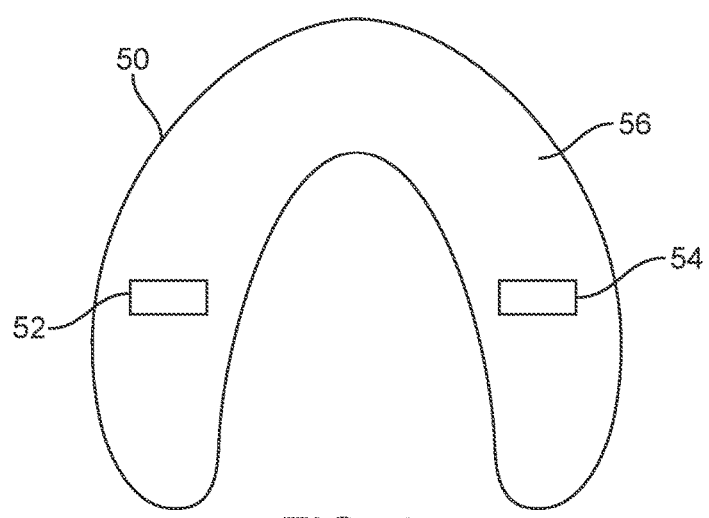
FIG. 4 shows a top view of an oral appliance formed with one or more slots to facilitate manufacturing.
Figure 5:
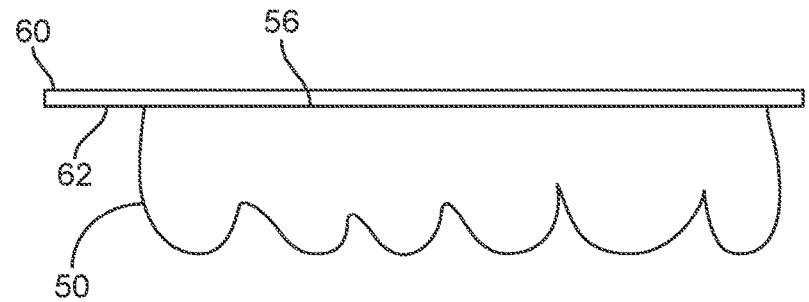
FIG. 5 shows a side view of an oral appliance mounted on a base for manufacturing.
Figure 6:
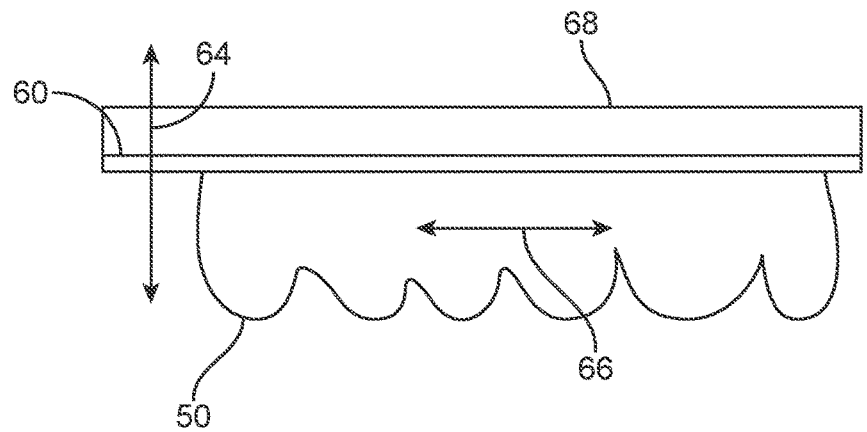
FIG. 6 shows a side view of the oral appliance and some of the directions that the appliance may be translated and/or rotated to facilitate trimming of the appliance.
Figure 7:
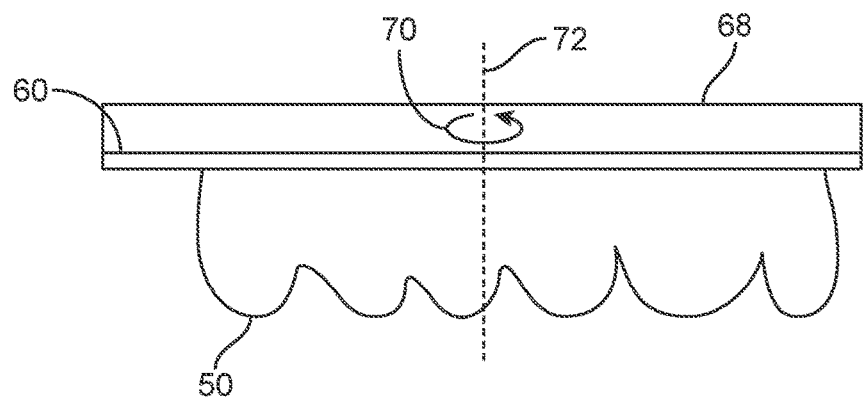
FIG. 7 shows a top view of a cutting device which may be used to trim the oral appliance and some of the directions that the cutting device may be articulated.

Once the mold has been formed with the base region 44, the mold may be further processed. A bottom view of a formed mold 50 is shown in FIG. 4 with slots 52, 54 formed into a surface 56 of the mold 50 into which tools or anchors can be inserted for securing the mold 50 in place during further processing procedures. FIG. 5, for example, shows a side view of the fabricated mold 50 secured along its interface surface 56 and anchored via slots 52, 54 to a surface 62 of a platform 60. FIG. 6 shows one configuration where the platform 60 holding the physical mold 50 for pressure-forming the oral aligner may be positioned upside down, i.e., such that the mold 50 is held in an inverted position as shown. The platform 60 may be fixed or secured upon a stage 68 which may be actuated to move the platform 60 and mold 50 in a vertical direction 64 (up/down) or linearly 66 within a plane defined by the stage 68 and platform 60, as shown in FIG. 6, to facilitate cutting or trimming processes for the mold 50. The stage 68 may also be actuated to rotate 70 the platform 60 and mold 50 within the plane defined by the stage 68 such that the stage 68 rotates about an axis which may be aligned to be collinear with a central axis 72 of the mold 50, as shown in FIG. 7.

Another configuration may position the stage 68 relative to a blade which may be translated and/or rotated relative to mold 50 and stage 68. The system may calculate each motion stage parameters and while the mold 50 is moved rotationally, the blade may be used to cut or trim the mold 50, as needed. This may involve rotating the model 50 around its center and calculating the blade tilt angle and blade height 16, as described above.

Yet another configuration may involve moving the stage 68 and mold 50 relative to a stationary blade such that the mold 50 is rotated, tilted, and/or translated by the stage 68 while the position of the blade remains unchanged. The system then adjusts different tools to trim the mold 50 at the pre-designated cutting path. In this or any other variation, the blade can include a mechanical blade or a laser cutting tool and software may be used to calculate the laser focus to easier move the source back and force or attenuate its power to focus and cut the mold 50 at designated locations.

Figure 8:
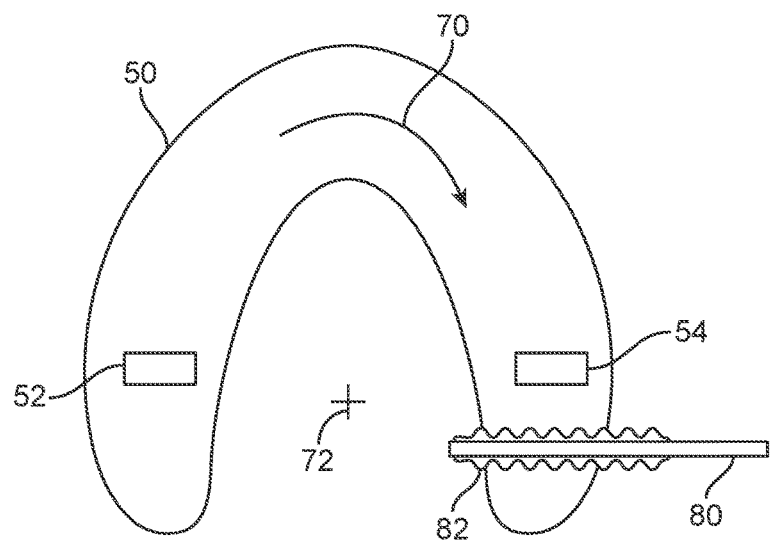
FIG. 8 shows a top view of an oral appliance and a cutting device for manufacturing.

In one implementation for processing the mold, FIG. 8 shows a top view of a mold 50 positioned upon a stage and rotated relative to a stationary cutting blade 80. The mold 50 may be secured to the underlying platform and stage and rotated within the plane of the platform in the direction 70 about its central axis 72 which may be coincident with the axis of rotation defined by the stage. The cutting blade 80 having a cutting edge 82 may be positioned relative to the mold at the predetermined height and angle relative to the mold 50, as described herein, to trim the mold 50 as it rotates.

In this variation, instead of generating a complex 3D cutting curve, the system simply uses a 2D flat curve by optionally setting a water mark cutting plane. The advantage is that no numerical controller is needed to cut the molds. Instead, the mold 50 can be simply placed by hand and rotated (e.g., manually or automatically), as shown, to push it through or past the cutting blade 80. The action may be similar to cutting a wood board with a circular motion rather than a straight or linear motion.

Another advantage of this configuration is the ability to utilize a separate fixture which can be used to sandwich the material forming the oral appliance after placement upon the mold, e.g., when thermal forming the oral appliance. The material from which the oral appliance is thermal formed, if used for fabrication, may be secured directly removing the need for yet another fixture on the mold itself. One implementation uses a two-dimensional (2D) laser cutting tool that can be used to cut along a flat curve formed by a horizontal silhouette line generated by a projection to the base surface.

Figure 9:
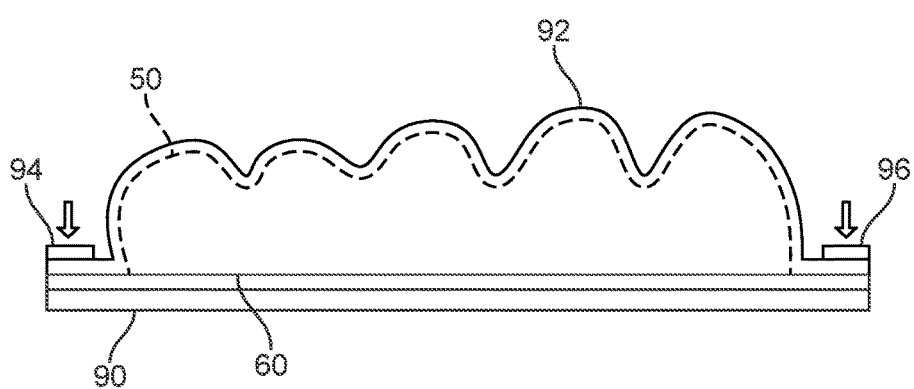
FIG. 9 shows a side view of an oral appliance secured to a base for processing.

FIG. 9 shows a side view of one embodiment where the mold 50 is positioned above a platform 60 with the plastic shell mold 92 after thermal forming upon the mold 50. The entire assembly of the mold 50, platform 60, and shell mold 92 rests on a flat bottom fixture base 90 having a clamping fixture with one or more clamping plates 94, 96 on either side to secure the mold 50 and shell mold 92. The fixture assembly may be used to secure the shell mold 92 for further processing such as trimming. Once the processing has been completed, the clamping plates 94, 96 may be released and the shell mold 92 and/or mold 50 may be removed from the fixture base 90.

Figure 10:
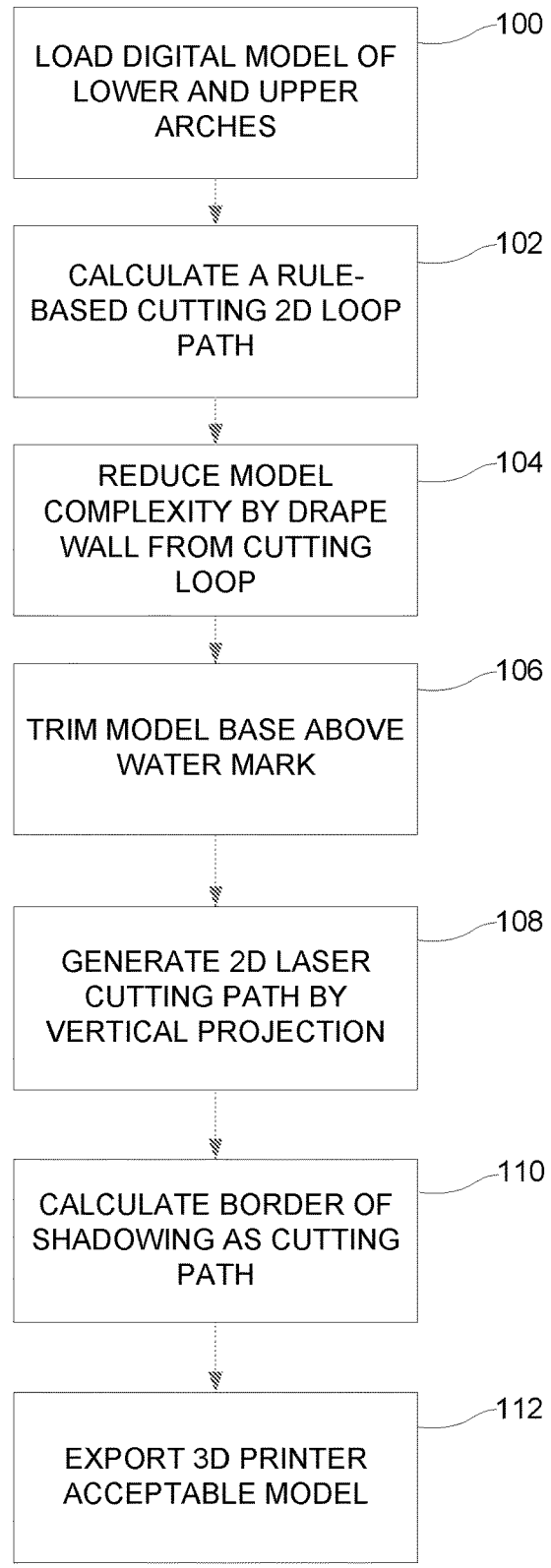
FIG. 10 shows an exemplary process for laser cutting a physical mold for the oral appliance.

In the event that the physical mold is processed by laser cutting, the steps shown in the flow diagram of FIG. 10 may be implemented in another embodiment. Initially, a digital model of the lower and upper arches may be loaded in the system 100, as described previously. The system may then calculate a rule based cutting loop path for the 2D cutting system 102, as discussed above. Model complexity may be reduced by applying the drape wall from the cutting loop 104, as also discussed above. The process trims the mold base above a water mark 106 which may be imprinted upon the mold to demarcate a boundary. For laser cutters, the system may generate a 2D laser cutting path using vertical projects 108 and determine the border of the shadow as the cutting path 110. The system may then export the 3D printer model 112 for fabrication. The process may be repeated for each subsequent mold used for fabricating one or more of the corresponding oral appliances.

Figure 11:
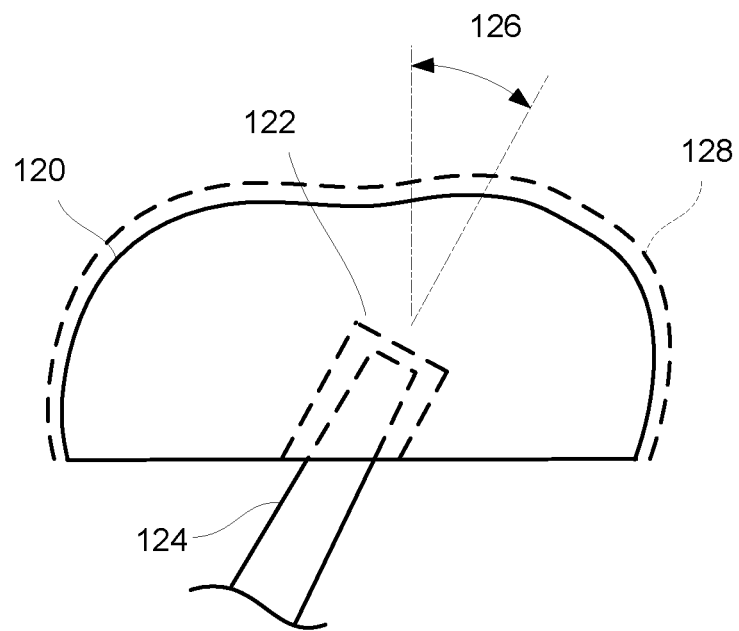
FIG. 11 shows a side view of an oral appliance formed with a tooling cavity to facilitate articulation of the oral appliance.

Regardless of how the mold is trimmed or how the oral appliance is processed upon the mold, the separation and release of the shell (aligner or oral appliance) from the mold can be generally difficult due to the lack of any features for grabbing the mold. To address this one or more holes or cavities 122 may be drilled or otherwise defined at various locations within the mold 120 and optionally at an angle 126 relative to a normal direction of the mold, as shown in the end view of FIG. 11. The angling of the hole or cavity 122 enables the insertion of a tool 124 which may be positioned within to provide a counterforce for releasing and removing an oral appliance 128 formed upon the mold 120.

Figure 12:
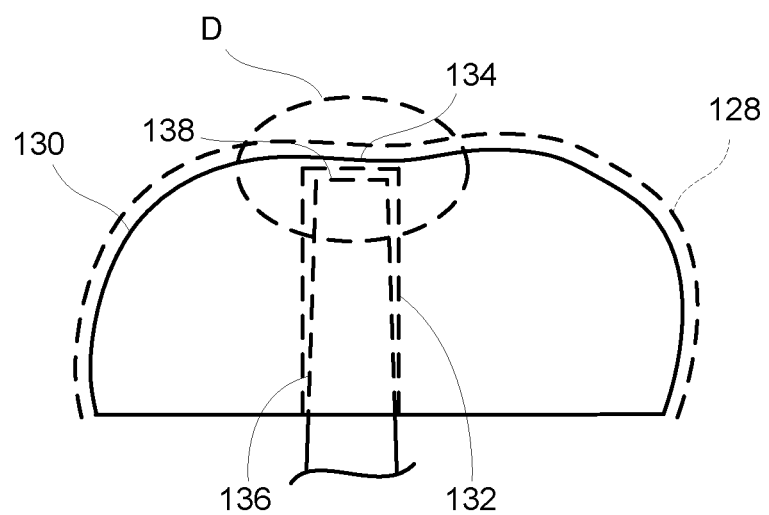
FIG. 12 shows a side view of another oral appliance having a region formed to facilitate removal of the appliance via a stream of air or gas.

Another embodiment shown in the end view of FIG. 12 which illustrates an end view of a mold 130 formed to have a hole or cavity 132 which extends through the bottom of the mold 130 and into proximity of the top of the mold, i.e., where the model of the patient's dentition is located. A thin layer 134 of the mold may extend over the hole 132 to provide a surface upon which the oral appliance 128 may be fabricated, as described herein. However, once fabrication of the oral appliance 128 has been completed and trimmed suitably, the tip 138 of a tool 136 appropriately sized may be inserted into the opening 132 and pushed through the thin layer 134 of the mold 130 and into contact against an inner surface of the oral appliance such that the oral appliance 128 may be urged to release from the mold 130. Alternatively, the tool 136 may comprise an air blower so that the tip 138 may be positioned within the opening 132 into proximity of the layer 134, as shown by the detail view D, where a jet of air introduced through tip 138 may be break through the layer 134 and urge the oral appliance 128 to release from the mold 130.

To ensure that the mold 130 retains its strength during fabrication of the mold, oral appliance, or release of the oral appliance from the mold, the mold 130 may be optionally fabricated to include a honeycomb, mesh, or other porous feature underlying the surface of the mold 130. With the added structural strength provided by a honeycomb or mesh, the layer 134 may be broken or punctured and still allow of the passage of the air but the mold 130 may have the structural resilience to withstand the pressures generated by the shell formation upon the mold 130 surface.

Figure 13:
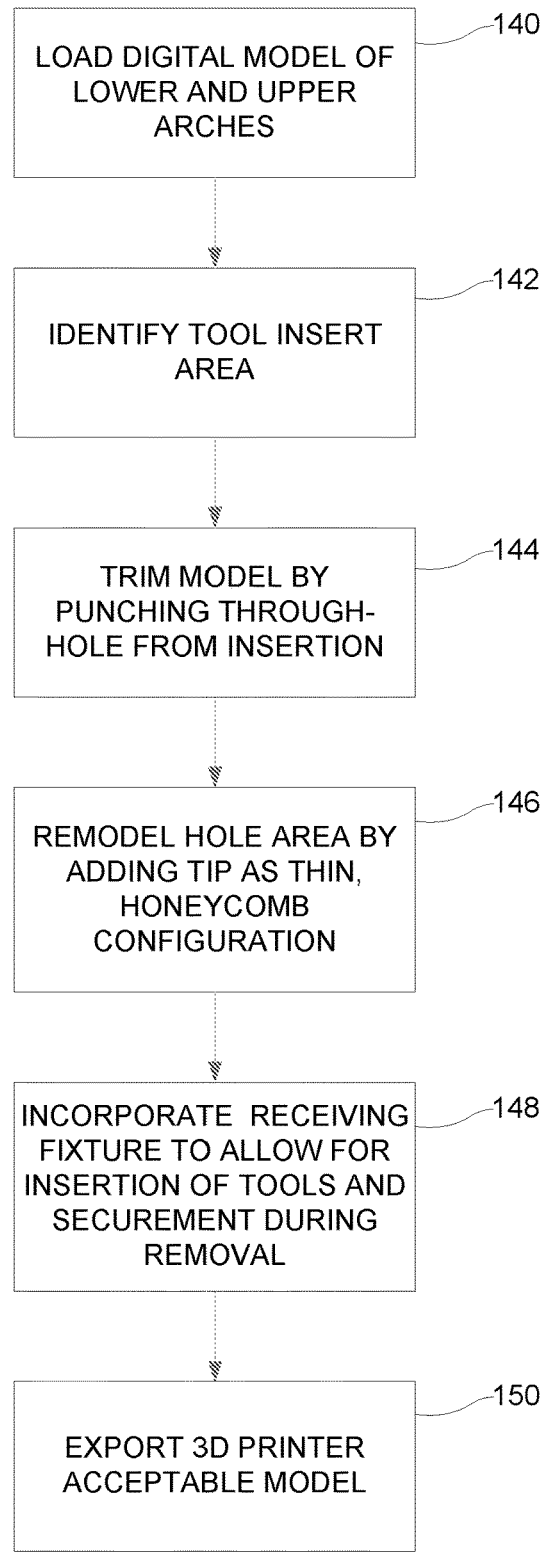
FIG. 13 shows an exemplary process for facilitating removal of the oral appliance.

FIG. 13 illustrates a flow diagram for removing the oral appliance fabricated upon a mold, as described above. As previously described, the digital model of the lower and upper arches may be loaded into the computer system 140. The system may then identify an appropriate area along the model for tool insertion 142. Such an area may be located away front the dentition model and so as not to interfere with the fabrication of the oral appliance upon the mold. The system may trim the model by defining a through-hole from insertion 144 and to strengthen the through-hole, the system may then remodel the hole area by forming the region of the hole adjacent to where the dentition is modeled as a mesh or honeycomb configuration 146 to provide strength to the model when fabricated but which still allows for air to pass through the openings defined by the mesh or honeycomb. The model may incorporate a receiving fixture to allow for the insertion of tools and/or allows for the securement of the mold during removal of the oral appliance from the mold 148. Once the model has been completed, a 3D printer acceptable model may be exported 150.

Figure 14:
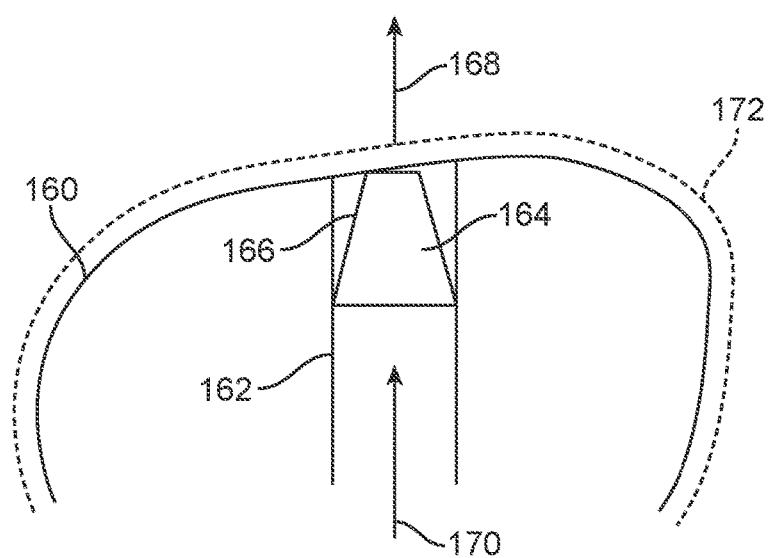
FIG. 14 shows a side view of another oral appliance having a cavity formed to facilitate its removal via a wedged removal member.

FIG. 14 shows yet another exemplary embodiment for facilitating removal of the fabricated oral appliance from the mold in the end view of mold 160. The mold 160 may be formed to define an opening or channel 162 which extends through the mold 160 from a bottom (e.g., opposite to the portion of the mold replicating the dentition) towards a top (e.g., portion of the mold replicating the dentition such as the occlusal surfaces). In this embodiment, a tapered structure 164 may be formed to be part of the oral appliance 172 which is formed upon the mold 160. The tapered structure 164 may remain attached to an internal surface of the oral appliance while being formed with a tapered surface 166 which tapers to a larger diameter structure within the opening or channel 162 away from the oral appliance 172.

The tapered structure 164, once formed, may present a cork-like structure which helps to secure the oral appliance upon the mold 160 during fabrication and processing. Once the oral appliance 172 is completed and ready for release and removal from the mold 160, a tool may be inserted into the opening or channel 162, in the direction 170 as indicated, and used to gently push against the bottom surface of the tapered structure 164 to urge the release of the oral appliance 172 from the mold 160 until the tapered structure 164 is removed entirely from the opening or channel 162, in the direction 168 as indicated. Once the oral appliance 172 has been removed entirely, the tapered structure 164 may be removed from the oral appliance 172 as well.

Figure 15:
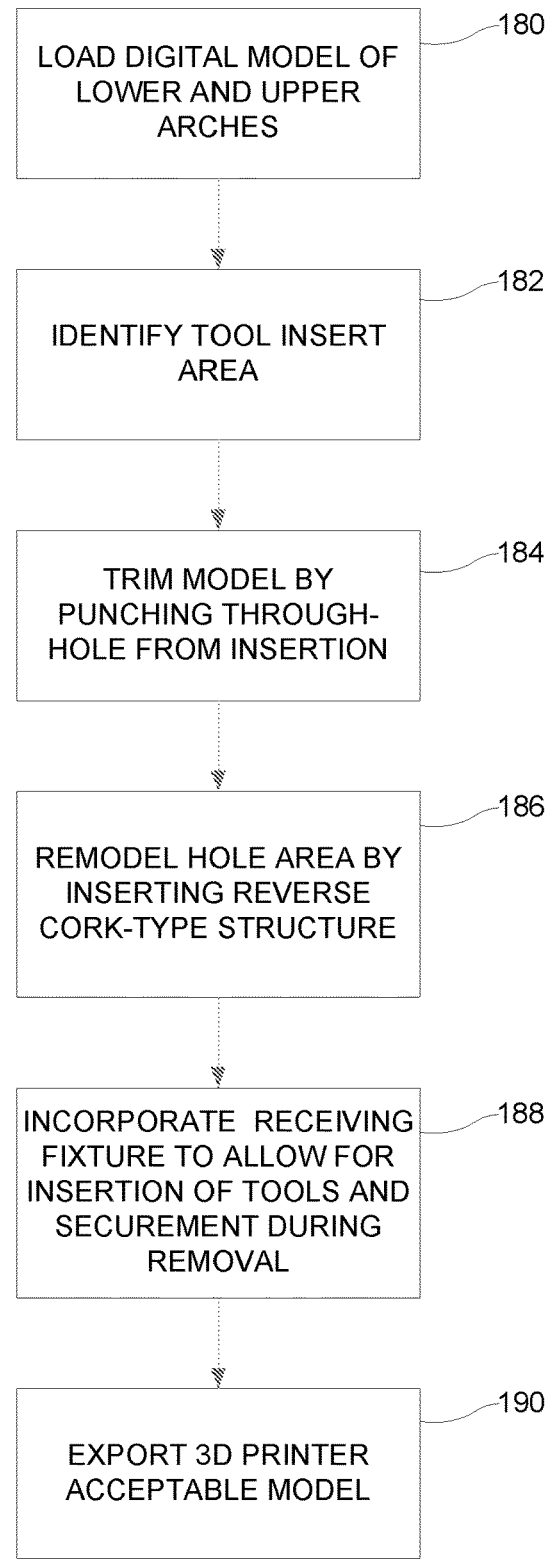
FIG. 15 shows an exemplary process for facilitating removal of the oral appliance via the wedged removal member.

FIG. 15 illustrates a flow diagram for removing the oral appliance fabricated upon a mold using the tapered structure 164, as described above. As previously described, the digital model of the lower and upper arches may be loaded into the computer system 180. The system may then identify an appropriate area along the model for tool insertion 182. Such an area may be located away from the dentition model and so as not to interfere with the fabrication of the oral appliance upon the mold. The system may trim the model by defining a through-hole from insertion 184 and to strengthen the through-hole, the system may then remodel the hole area by forming or inserting the tapered structure 164 (e.g., reverse cork-type structure) 186. The model may incorporate a receiving fixture to allow for the insertion of tools and/or allows for the securement of the mold during removal 188 of the oral appliance from the mold. Once the model has been completed, a 3D printer acceptable model may be exported 190.

The system or method described herein may be deployed in part or in whole through a computer system or machine having one or more processors that execute software programs with the methods as described herein. The software programs may be executed on computer systems such as a server, domain server. Internet server, intranet server, and other variants such as secondary server, host server, distributed server, or other such computer or networking hardware on a processor. The processor may be a part of a server, client, network infrastructure, mobile computing platform, stationary computing platform, or other computing platform. The processor may be any kind of computational or processing device capable of executing program instructions, codes, binary instructions or the like that may directly or indirectly facilitate execution of program code or program instructions stored thereon. In addition, other devices required for execution of methods as described in this application may be considered as a part of the infrastructure associated with the computer system or server.

The system or method described herein may be deployed in part or in whole through network infrastructures. The network infrastructure ma include elements such as computing devices, servers, routers, hubs, firewalls, clients, wireless communication devices, personal computers, communication devices, routing devices, and other active and passive devices, modules or components as known in the art. The computing or non-computing device(s) associated with the network infrastructure may include, apart from other components, a storage medium such as flash memory, buffer, stack, RAM, ROM, or the like. The processes, methods, program codes, and instructions described herein and elsewhere may be executed by the one or more network infrastructural elements.

The elements described and depicted herein, including flow charts, sequence diagrams, and other diagrams throughout the figures, imply logical boundaries between the elements. However, according to software or hardware engineering practices, the depicted elements and the functions thereof may be implemented on machines through the computer executable media having a processor capable of executing program instructions stored thereon and all such implementations may be within the scope of this document. Thus, while the foregoing drawings and descriptions set forth functional aspects of the disclosed methods, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this document. As such, the depiction or description of an order for various steps should not be understood to require a particular order of execution for those steps, unless required by a particular application, or explicitly stated or otherwise clear from the context.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device, or other hardware. All such permutations and combinations are intended to fall within the scope of the present disclosure.

The applications of the devices and methods discussed above are not limited to the dental applications but may include any number of further treatment applications. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method of forming an oral appliance, comprising:
receiving a digital model of a patient's dentition;
calculating a rule-based cutting loop path on the model for determining a path for trimming a mold replicating the patient's dentition;
applying a drape wall from the cutting loop on the model to reduce a complexity of the model;
determining a position of a cutting instrument relative to the mold for trimming the mold;
generating a computer numerical control code based on the drape wall and position of the cutting instrument; and
fabricating the mold based on the generated computer numerical control code.

2. The method of claim 1 wherein calculating a rule-based cutting loop path comprises identifying a first location and a second location opposite to the first location on the model at corresponding interface regions and extending a trim line between the first location and second location.

3. The method of claim 2 wherein applying a drape wall comprises identifying the trim line and replacing a volume below the trim line with a base region.

4. The method of claim 1 wherein the drape wall comprises a base region having straightened lines.

5. The method of claim 1 wherein the drape wall comprises a base region having a tapered surface.

6. The method of claim 1 wherein applying a drape wall comprises limiting a height of the drape wall to avoid stretching an oral appliance formed upon the mold.

7. The method of claim 1 wherein fabricating the mold comprises securing the mold to a platform.

8. The method of claim 7 further comprising securing the mold and platform upon one or more stages.

9. The method of claim 8 further comprising rotating the mold relative to the cutting instrument.

10. The method of claim 8 further comprising rotating the cutting instrument relative to the mold.

11. The method of claim 1 wherein determining a position of a cutting instrument further comprises generating a 2D cutting path by setting a water mark cutting plane.

12. The method of claim 1 wherein fabricating the mold further comprises placing an opening or hole on a base of the mold for receiving a tool to facilitate removal of an oral appliance from the mold.

13. The method of claim 12 wherein placing an opening or hole comprises placing the opening or hole at an angle.

14. The method of claim 12 further comprising applying a stream of air to the opening or hole such that the oral appliance is released from the mold.

15. The method of claim 12 further comprising forming a tapered structure within the opening or hole to facilitate removal of the oral appliance from the mold.

16. The method of claim 1 wherein fabricating the mold further comprises applying the cutting instrument across an inner and outer arch curve of the mold.

17. A method of forming an oral appliance, comprising:
receiving a digital model of a patient's dentition;
calculating a rule-based cutting loop path on the model for determining a path for trimming a mold replicating the patient's dentition;
applying a drape wall from the cutting loop on the model to reduce a complexity of the model;
determining a predetermined height of a base of the model;
generating a computer numerical control code of the model; and fabricating the mold based on the generated computer numerical control code.

18. The method of claim 17 further comprising determining a position of a cutting instrument relative to the mold for trimming the mold prior to fabricating the mold.

19. The method of claim 18 wherein generating a computer numerical control code further comprises generating the computer numerical control code based on the drape wall and position of the cutting instrument.

20. The method of claim 17 wherein calculating a rule-based cutting loop path comprises identifying a first location and a second location opposite to the first location on the model at corresponding interface regions and extending a trim line between the first location and second location.

21. The method of claim 20 wherein applying a drape wall comprises identifying the trim line and replacing a volume below the trim line with a base region.

22. The method of claim 17 wherein fabricating the mold comprises securing the mold to a platform.

23. The method of claim 22 further comprising securing the mold and platform upon one or more stages.

24. The method of claim 23 further comprising rotating the mold relative to the cutting instrument.

25. The method of claim 17 wherein fabricating the mold further comprises placing an opening or hole on a base of the mold for receiving a tool to facilitate removal of an oral appliance from the mold.

26. The method of claim 25 further comprising forming a tapered structure within the opening or hole to facilitate removal of the oral appliance from the mold.

27. The method of claim 17 wherein fabricating the mold further comprises applying the cutting instrument across an inner and outer arch curve of the mold.

* * * * *